United States Patent
Haimerl

(10) Patent No.: US 9,572,630 B2
(45) Date of Patent: Feb. 21, 2017

(54) PLANNING ASSISTANCE FOR CORRECTING JOINT ELEMENTS

(75) Inventor: Martin Haimerl, Gilching (DE)

(73) Assignee: Brainlab AG, Munich (DE)

( * ) Notice: Subject to any disclaimer, the term of this patent is extended or adjusted under 35 U.S.C. 154(b) by 941 days.

(21) Appl. No.: 12/542,102

(22) Filed: Aug. 17, 2009

(65) Prior Publication Data
US 2010/0049493 A1 Feb. 25, 2010

Related U.S. Application Data

(60) Provisional application No. 61/092,204, filed on Aug. 27, 2008.

(30) Foreign Application Priority Data

Aug. 20, 2008 (EP) ................................. 08162678

(51) Int. Cl.
*A61B 5/05* (2006.01)

(52) U.S. Cl.
CPC .............. *A61B 90/36* (2016.02); *A61B 34/10* (2016.02); *A61B 2034/2068* (2016.02); *A61B 2090/364* (2016.02); *A61B 2090/378* (2016.02)

(58) Field of Classification Search
CPC . A61B 19/52; A61B 19/50; A61B 2019/5289; A61B 2019/5276; A61B 2019/5268
USPC ............ 600/427, 424, 439; 606/102; 703/11
See application file for complete search history.

(56) References Cited

U.S. PATENT DOCUMENTS

| | | | |
|---|---|---|---|
| 6,205,411 B1 | 3/2001 | DiGioia, III et al. | |
| 6,711,432 B1 | 3/2004 | Krause et al. | |
| 7,618,451 B2 * | 11/2009 | Berez et al. ............... | 623/14.12 |
| 2006/0084867 A1 * | 4/2006 | Tremblay ............... | A61B 90/36 600/434 |
| 2006/0204067 A1 * | 9/2006 | Tuma et al. .................. | 382/128 |
| 2007/0156157 A1 * | 7/2007 | Nahum et al. ................ | 606/130 |
| 2007/0198022 A1 * | 8/2007 | Lang .................... | A61B 17/154 606/88 |
| 2007/0249967 A1 * | 10/2007 | Buly et al. ..................... | 600/595 |
| 2008/0033442 A1 * | 2/2008 | Amiot et al. ................... | 606/80 |
| 2008/0161680 A1 * | 7/2008 | von Jako et al. ............. | 600/424 |
| 2008/0194997 A1 * | 8/2008 | Zhang .......................... | 600/595 |

FOREIGN PATENT DOCUMENTS

EP     1 800 616 A1    6/2007

OTHER PUBLICATIONS

Tannast et al., "Noninvasive Three-Dimensional Assessment of Femoroacetabular Impingement", Journal of Orthopaedic Research, vol. 25, No. 1, 2007, pp. 122-131.

* cited by examiner

*Primary Examiner* — Joel Lamprecht
(74) *Attorney, Agent, or Firm* — Tucker Ellis LLP

(57) ABSTRACT

A planning assistance method for correcting joint elements is provided. In accordance with the method, the actual shape of at least one part of the joint element which is of interest is detected. The actual shape is compared with an intended shape, and the comparison data is used to plan the abrasion of joint element parts.

16 Claims, 1 Drawing Sheet

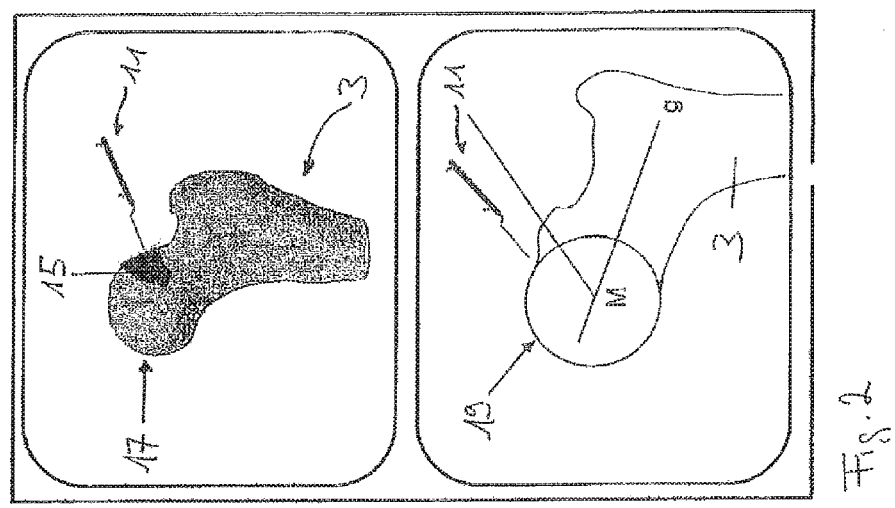
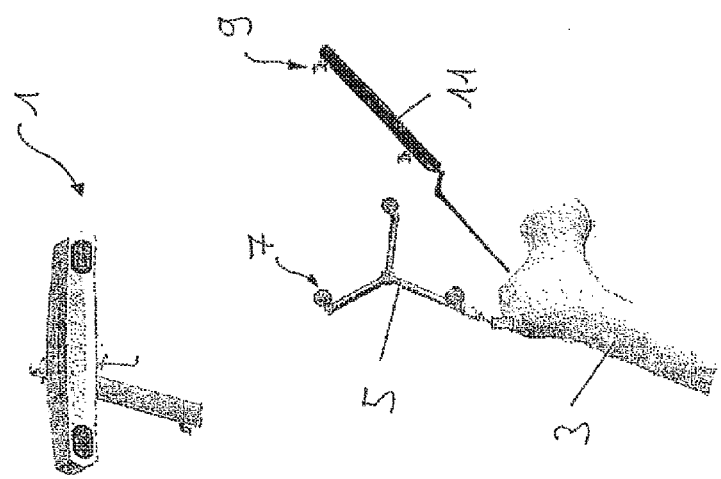

PLANNING ASSISTANCE FOR CORRECTING JOINT ELEMENTS

RELATED APPLICATION DATA

This application claims the priority of U.S. Provisional Application No. 61/092,204, filed on Aug. 27, 2008, which is hereby incorporated in its entirety by reference.

FIELD OF THE INVENTION

The invention relates to planning assistance for correcting joint elements and/or joint bones.

BACKGROUND OF THE INVENTION

Changes in the shape of joint bones are a possible cause of arthritic joint diseases. Bone anomalies can for example occur in the region of the hip joint which lead to bone collisions in the joint region when the leg moves and—in particular in the longer term—cause attrition complaints. In surgical correcting steps, the femoral head or acetabular rim—both are examples of joint elements in the terminology of the present invention—are for example returned back to their natural shape in order to prevent collisions between the femur and the acetabulum in the joint region, wherein the intention is to restore the natural shape of the femoral head.

In open (non-arthroscopic) surgeries, spherical templates are sometimes used in accordance with the prior art in order to check the sphericity of the femoral head. Using these and other currently used means, it is not possible to systematically compare the desired state with the current shape of the joint element accurately. In particular, it is not possible to monitor and control the abrasion depth to the necessary and desired level of accuracy.

SUMMARY OF THE INVENTION

It is therefore an object of the present invention to provide a planning assistance method for correcting joint elements which optimizes the correction and restoration of joint elements. The intention is in particular to provide navigation assistance, i.e. planning assistance, which enables the abrasion depth to be navigated.

This object is solved by a planning assistance method for correcting joint elements, in which: the actual shape of at least one part of the joint element which is of interest is detected and read-in and/or stored with the assistance of a computer; the actual shape is compared with the intended shape, with the assistance of a computer; and the comparison data is used to plan—with the assistance of a computer—the abrasion of joint element parts which are to be ablated. The sub-claims define preferred embodiments of the invention.

In general terms, the invention is thus a planning assistance method for correcting joint elements, in which:
- the actual shape of at least one part of the joint element which is of interest is detected and read-in and/or stored with the assistance of a computer;
- the actual shape is compared with the intended shape, with the assistance of a computer; and
- the comparison data, in particular the deviations between the actual shape and the intended shape, are used to plan—with the assistance of a computer—the abrasion of joint element parts which are to be ablated.

By comparing the shapes and incorporating the result of this into the computer-assisted planning, the requirements for a high level of accuracy which are necessary in order to navigate the abrasion depth are fulfilled, i.e. the invention provides a special technique for checking the actual shape during the abrasion procedure and thus provides a navigation which can check the contour fidelity, for example the sphericity of the femoral head, within the joint region. Using this check, it is then possible to correctly assess the correct abrasion depth. A good post-operative shape is necessary for the longer-term success of the surgery, and an accurate abrasion navigation in accordance with the present invention therefore provides a major advantage for a surgeon, and specifically for surgeons with little experience.

In other words, the invention provides a way of intra-operatively checking contours on joint element surfaces which are to be processed and thus goes beyond conventional navigation, which merely uses previously acquired data (for example MR data or CT data) as a basis for the entire operation.

According to the present invention, the actual shape is detected and/or acquired by means of an instrument which can be positionally determined with the aid of a medical navigation and tracking system and which can in particular be a navigated and tracked pointer.

In very general terms, the actual shape can be two-dimensionally or three-dimensionally detected by such a navigated instrument.

Another embodiment variant ascertains the actual shape using specific geometric properties, without completely reconstructing a three-dimensional shape, namely from navigation data such as acquired points, wherein specifically surface normals or the curvature on different parts of the joint element surface are reconstructed.

It is also possible to ascertain the actual shape using navigated and/or tracked pointers which scan the joint surface at more than one point, in particular at three points. It is in principle also possible to scan linearly or over an area (for example, on various partial areas). In one embodiment, such pointers are templates, specifically navigated and/or tracked curvature templates, spherical templates or soft templates which generate a negative imprint of the joint bone surface.

Within the framework of the invention, the intended shape is preferably determined by means of prior-known information, in particular from:
- acquired patient data;
- model data, target shapes or predetermined shapes for the joint element;
- generic shapes, such as approximated spheres; or from a combination of two or more of these types of information.

The invention also relates to a program which, when it is running on a computer or is loaded on a computer, causes the computer to perform a method such as has been described above in various embodiments. It also relates to a computer program storage medium which comprises such a program.

BRIEF DESCRIPTION OF THE DRAWINGS

The invention is explained in more detail below on the basis of embodiments and with the aid of the enclosed drawings. It can include any of the features described here, individually and in any combination. The invention can in particular also be interpreted as a device or system of individual devices, wherein the devices and/or device parts then fulfill the functions which are described here in terms of a method, and the combination of the device and/or device parts then forms the corresponding invention. The same applies to the use of such devices and/or device parts and of specific method steps within the framework of applications in accordance with the invention.

FIG. 1 shows a navigation environment for the planning assistance in accordance with the invention.

FIG. 2 shows examples of image displays within the framework of navigation and/or planning assistance in accordance with the invention.

DETAILED DESCRIPTION

In one embodiment of the invention, the current bone structure (during the abrasion process) is acquired by a pointer, and the shape obtained is compared with the desired bone shape, wherein a reconstruction of the current bone shape should be performed, and this reconstruction can be assisted by known information (for example the desired shape, model knowledge, or a generic shape such as for example an approximated sphere). FIG. 1 shows the navigation environment which is used for this embodiment. The navigation system comprises a camera array 1, the navigation hardware 2 (only shown schematically) and a reference array 5 which is rigidly connected to the upper leg bone (femur) 3. Three passive spherical markers 7 are situated on the reference array 5 and are detected by the camera system 1, such that the spatial position of the bone 3 can be determined via the reference array 5 using the navigation system. A pointer 11, i.e. a medical pointing device, which can also be seen in FIG. 1, is likewise positionally followed, i.e. tracked, via the navigation. To this end, the pointer 11 comprises the two spherical markers 9. The position of the tip of the pointer 11 can be determined at any time due to pre-calibration or by using a pre-calibrated instrument.

This latter circumstance can then be used to detect the actual shape of a femoral head during an abrasion operation. With the aid of the data thus captured, it is then possible to reconstruct the current bone shape in the navigation system, and on the basis of this current bone shape, the necessary abrasion depth can always be promptly determined at any point of the joint bone, such that abrasion will be performed reliably and only at the necessary points, and a successful operation is guaranteed to a large extent.

Detecting the actual shape of the bone, reconstructing the bone and navigating the abrasion depth will now be explained in somewhat more detail on the basis of the representation in FIG. 2, which shows sample screen displays of a navigation system (output on the navigation screen 4).

The upper display in FIG. 2, for example, shows an area 15 on the femoral head 17 of the femur 3 being detected by using a pointer 11.

The lower display of the display device 4 in FIG. 2 shows how model data and/or generic inscribed shapes can be used in accordance with the invention. The pointer 11 is superimposed in its actual position, in which its tip is placed on a protrusion of bone on the femoral head. The desired shape of the femoral head is superimposed and reconstructed in the navigation as a sphere 19, wherein the neck axis g and the mid-point M placed on it are used for displaying and positioning the sphere. In the present case, the system will indicate that the tip of the pointer 11 is still situated at a certain distance above the circular line 19, for example about 1.5 mm, and the current abrasion depth at the point traveled to by the tip follows directly from this information.

Lastly, it may also be noted that other embodiments are possible which take into account the principles of detecting the shape in accordance with the invention but use special devices for acquiring data on the bone surface. These devices can include:

robot-assisted acquisition of surface points, wherein the robot or a telemanipulator can be used as a navigation device. The system can be fixed to the bone (for example by a special type of clamp), and the remaining (relative) motion has to be recorded. This should increase the (relative) level of accuracy;

special hardware devices for acquiring information on the sphericity/curvature of the bone surface at a particular point. Tracked and/or navigated, spherical templates or pointers comprising specific geometric structures can for example be used. Soft templates, which generate a negative imprint of the bone surface, can also be used. Another example of a special hardware device would be a pointer comprising at least three tips for acquiring the surface orientation at a particular position. The three tips have to be positioned on the surface during acquisition, and their orientation can then be determined from the orientation of the handle of the pointer.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A planning assistance method for restoring joint elements to an intended, natural shape, the method comprising:

determining an actual shape of a joint surface of a joint element of interest, wherein the determining the actual shape comprises drawing a tip of a navigated and tracked pointer across the joint surface, the navigated and tracked pointer being configured to be positionally determined by an associated medical navigation and tracking system; and using a computer:
comparing the actual shape of the joint surface of the joint element as determined by using the pointer, with an intended, natural shape of the joint surface of the joint element;
planning an abrasion of a portion of the joint element based on the comparing, wherein the abrasion defines the intended, natural shape of the joint surface of the joint element; and
generating an output signal representative of the plan.

2. The method according to claim 1, wherein the comparing comprises determining deviations between the actual shape and the intended shape.

3. The method according to claim 1, further comprising abrading the joint based on the plan.

4. The method according to claim 1, wherein the determining the actual shape comprises using specific geometric properties, without completely reconstructing a three-dimensional shape.

5. The method according to claim 4, wherein the determining the actual shape comprises reconstructing surface normals or the curvature on different parts of the joint element surface.

6. The method according to claim 4, wherein the using specific geometric properties comprises using acquired points or endoscopic images.

7. The method according to claim 1, wherein the determining the actual shape comprises using an image acquisition device intra-operatively to determine the actual shape.

8. The method according to claim 7, wherein the using the image acquisition device comprises using ultrasound probes or remote scanners.

9. The method according to claim 8, wherein the using the remote scanners comprises using laser scanners.

10. The method according to claim 1, wherein the determining the actual shape includes acquiring surface points via robot-assistance or telemanipulator-assistance.

11. The method according to claim 1, wherein the determining the actual shape of the joint surface of the joint element of interest comprises drawing the tip of the navigated and tracked pointer across at least three points of the joint surface.

12. The method according to claim 11, wherein the drawing the tip of the pointer comprises determining the actual shape of the joint surface of the joint element of interest using pointers formed as templates.

13. The method according to claim 12, wherein the using pointers formed as templates comprises using navigated and/or tracked curvature templates, spherical templates or soft templates which generate a negative imprint of the joint surface.

14. The method according to claim 1, further comprising determining the intended shape based on prior-known information.

15. The method according to claim 14, wherein the determining the intended shape based on the prior-known information comprises using at least one of:
acquired patient data;
model data, target shapes or predetermined shapes for the joint element; or
generic shapes, such as approximated spheres.

16. A non-transitory computer readable storage medium storing a program which, when running on an associated computer or loaded onto the associated computer, causes the associated computer to perform a planning assistance method for restoring joint elements to an intended, natural shape, comprising:

determining an actual shape of a joint surface of a joint element of interest, wherein the determining the actual shape comprises drawing a tip of a navigated and tracked pointer across the joint surface, the navigated and tracked pointer being configured to be positionally determined by an associated medical navigation and tracking system;

comparing the actual shape of the joint surface of the joint element as determined by using the pointer, with an intended, natural shape of the joint surface of the joint element;

using the computer, planning an abrasion of a portion of the joint element based on the comparing, wherein the abrasion defines the intended, natural shape of the joint surface of the joint element; and generating, by the associated computer, an output signal representative of the plan.

* * * * *